United States Patent
Jalett et al.

(10) Patent No.: US 6,822,118 B1
(45) Date of Patent: Nov. 23, 2004

(54) PROCESS FOR THE HYDROGENATION OF IMINES

(75) Inventors: Hans-Peter Jalett, Dornach (CH); Felix Spindler, Starrkirch-Wil (CH); Hans-Ulrich Blaser, Ettingen (CH); Reinhard Georg Hanreich, Basle (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 1613 days.

(21) Appl. No.: 08/926,835

(22) Filed: Sep. 10, 1997

Related U.S. Application Data

(63) Continuation of application No. 08/532,779, filed as application No. PCT/EP95/00221 on Sep. 29, 1995, now abandoned.

(30) Foreign Application Priority Data

Feb. 2, 1994 (CH) ................................................ 309/94

(51) Int. Cl.$^7$ ....................... C07C 233/05; C07C 209/38
(52) U.S. Cl. ....................... 564/211; 564/212; 564/248; 564/271; 564/398; 564/415; 549/68
(58) Field of Search ................................ 564/211, 212, 564/248, 271, 398, 415; 549/68

(56) References Cited

U.S. PATENT DOCUMENTS

| 4,994,615 A | | 2/1991 | Spindler et al. ............ 564/304 |
|---|---|---|---|
| 5,002,606 A | | 3/1991 | Moser et al. ................. 71/118 |
| 5,011,995 A | | 4/1991 | Pugin et al. ................. 564/302 |
| 5,103,061 A | * | 4/1992 | Blackborow et al. ....... 564/472 |
| 5,112,999 A | | 5/1992 | Osborn et al. ................ 556/23 |
| 5,202,473 A | | 4/1993 | Chan et al. ................. 562/496 |
| 5,210,202 A | * | 5/1993 | Petit et al. .................. 548/112 |
| 5,371,256 A | | 12/1994 | Togul et al. .................. 556/14 |
| 5,426,223 A | * | 6/1995 | Burk .......................... 564/150 |
| 5,859,300 A | * | 1/1999 | Jalett et al. ................. 564/143 |
| 5,886,225 A | * | 3/1999 | Jalett et al. ................. 564/415 |

FOREIGN PATENT DOCUMENTS

| EP | 0115470 | 8/1984 |
|---|---|---|
| EP | 0564406 | 10/1993 |
| WO | WO/A9215400 | 9/1992 |

OTHER PUBLICATIONS

Chao et.al., Tetrahedron Asymmetry, vol. 3, No. 3, pp 337–340, 1992.*
Henri B. Kagar, Chiral Ligands for Asymmetric Catalysis, vol. 5, pp 13–23, (1985).
Iamia Hayashi et al., Bull. Chem. Soc. Japan, vol. 53, pp 1136–1151 (1980).

* cited by examiner

*Primary Examiner*—Shailendra Kumar
(74) *Attorney, Agent, or Firm*—Rose M. Allen

(57) ABSTRACT

A process for the hydrogenation of imines with hydrogen under elevated pressure in the presence of iridium catalysts and with or without an inert solvent, wherein the reaction mixture contains an ammonium or metal chloride, bromide or iodide and additionally an acid.

37 Claims, No Drawings

PROCESS FOR THE HYDROGENATION OF IMINES

This application is a continuation of application Ser. No. 08/532,779, filed Sep. 29, 1995 now abandoned; which is a 371 of PCT/EP95/00221, filed Jan. 21, 1995.

The present invention relates to a process for the hydrogenation of imines with hydrogen under elevated pressure in the presence of iridium catalysts and a halide, wherein the reaction mixture contains an inorganic or organic acid.

U.S. Pat. No. 4,994,615 describes a process for the asymmetric hydrogenation of prochiral N-arylketimines wherein iridium catalysts having chiral diphosphine ligands are used. U.S. Pat. No. 5,011,995 describes a process for the asymmetric hydrogenation of prochiral N-alkylketimines using the same catalysts. U.S. Pat. No. 5,112,999 discloses polynuclear iridium compounds and a complex salt of iridium, which contain diphosphine ligands, as catalysts for the hydrogenation of imines.

Those homogeneous catalysis processes have proved valuable, although it is evident, especially in the case of relatively large batches or on an industrial scale, that the catalysts frequently tend to become deactivated to a greater or lesser extent depending on the catalyst precursor, the substrate and the diphosphine ligands that are used. In many cases, especially at elevated temperatures—for example at temperatures >25° C., which are necessary for a short reaction time—it is not possible to achieve complete conversion. For industrial applications of the hydrogenation process, therefore, the catalyst productivity is too low from the point of view of economic viability.

It has now been found, surprisingly, that the catalyst activity can be increased by a factor of 10 or more if the reaction mixture essentially contains a halide and also contains an acid. It has also unexpectedly been found that at the same time the deactivation of the catalysts can be considerably reduced or completely eliminated. It has also been found, surprisingly, that the enantioselectivity under the chosen conditions is high, and high optical yields of, for example, up to 80% can be achieved, even at reaction temperatures of more than 50° C.

The invention relates to a process for the hydrogenation of imines with hydrogen under elevated pressure in the presence of iridium catalysts and with or without an inert solvent, wherein the reaction mixture contains an ammonium chloride, bromide or iodide, or a metal chloride, bromide or iodide that is soluble in the reaction mixture, the metal preferably being an alkali metal, and additionally contains an acid.

Suitable imines are especially those that contain at least one

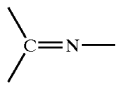

group. If the groups are substituted asymmetrically and are thus compounds having a prochiral ketimine group, it is possible in the process according to the invention for mixtures of optical isomers or pure optical isomers to be formed if enantioselective or diastereoselective iridium catalysts are used. The imines may contain further chiral carbon atoms. The free bonds in the above formulae may be saturated with hydrogen or organic radicals having from 1 to 22 carbon atoms or organic hetero radicals having from 1 to 20 carbon atoms and at least one hetero atom from the group O, S, N and P. The nitrogen atom of the group

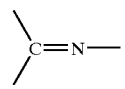

may also be saturated with $NH_2$ or a primary amino group having from 1 to 22 carbon atoms or a secondary amino group having from 2 to 40 carbon atoms. The organic radicals may be substituted, for example, by F, Cl, Br, $C_1$–$C_4$haloalkyl wherein halogen is preferably F or Cl, —CN, —$NO_2$, —$CO_2H$, —$CONH_2$, —$SO_3H$, —$PO_3H_2$, or $C_1$–$C_{12}$alkyl esters or amides, or by phenyl esters or benzyl esters of the groups —$CO_2H$, —$SO_3H$ and —$PO_3H_2$. Aldimine and ketimine groups are especially reactive, with the result that using the process according to the invention it is possible selectively to hydrogenate

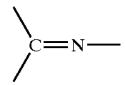

groups in addition to the

and/or

groups. Aldimine and ketimine groups are also to be understood to include

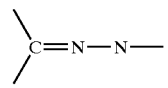

hydrazone groups.

The process according to the invention is suitable especially for the hydrogenation of aldimines, ketimines and hydrazones with the formation of corresponding amines and hydrazines, respectively. The ketimines are preferably N-substituted. It is preferable to use chiral iridium catalysts and to hydrogenate enantiomerically pure, chiral or prochiral ketimines to prepare optical isomers, the optical yields (enantiomeric excess, ee) being, for example, higher than 30%, preferably higher than 50%, and yields of more than 90% being achievable. The optical yield indicates the ratio of the two stereoisomers ford, which ratio may be, for example, greater than 2:1 and preferably greater than 4:1.

The imines are preferably imines of formula I

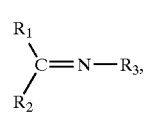

(I)

which are hydrogenated to form amines of formula II

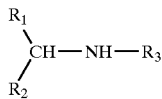

(II)

wherein
  R₃ is preferably a substituent and wherein
  R₃ is linear or branched $C_1$–$C_{12}$alkyl, cycloalkyl having from 3 to 8 ring carbon atoms; heterocycloalkyl bonded via a carbon atom and having from 3 to 8 ring atoms and 1 or 2 hetero atoms from the group O, S and NR₆; a $C_7$–$C_{16}$aralkyl bonded via an alkyl carbon atom or $C_1$–$C_{12}$alkyl substituted by the mentioned cycloalkyl or heterocycloalkyl or heteroaryl;
  or wherein
  R₃ is $C_6$–$C_{12}$aryl, or $C_4$–$C_{11}$heteroaryl bonded via a ring carbon atom and having 1 or 2 hetero atoms in the ring, R₃ being unsubstituted or substituted by —CN, —NO₂, F, Cl, $C_1$–$C_{12}$alkyl, $C_1$–$C_{12}$alkoxy, $C_1$–$C_{12}$alkylthio, $C_1$–$C_6$haloalkyl, —OH, $C_6$–$C_{12}$-aryl or -aryloxy or -arylthio, $C_7$–$C_{16}$-aralkyl or -aralkoxy or -aralkylthio, secondary amino having from 2 to 24 carbon atoms, —CONR₄R₅ or by —COOR₄, and the aryl radicals and the aryl groups in the aralkyl, aralkoxy and aralkylthio in turn being unsubstituted or substituted by —CN, —NO₂, F, Cl, $C_1$–$C_4$-alkyl, -alkoxy or -alkylthio, —OH, —CONR₄R₅ or by —COOR₄;
  R₄ and R₅ are each independently of the other hydrogen, $C_1$–$C_{12}$alkyl, phenyl or benzyl, or R₄ and R₅ together are tetra- or penta-methylene or 3-oxapentylene;
  R₆ has independently the same meaning as given for R₄;
  R₁ and R₂ are each independently of the other a hydrogen atom, $C_1$–$C_{12}$alkyl or cycloalkyl having from 3 to 8 ring carbon atoms, each of which is unsubstituted or substituted by —OH, $C_1$–$C_{12}$alkoxy, phenoxy, benzyloxy, secondary amino having from 2 to 24 carbon atoms, —CONR₄R₅ or by —COOR₄; $C_6$–$C_{12}$aryl or $C_7$–$C_{16}$aralkyl that is unsubstituted or substituted as R₃, or —CONR₄R₅ or —COOR₄, wherein R₄ and R₅ are as defined hereinbefore; or
  R₃ is as defined hereinbefore and R₁ and R₂ together are alkylene having from 2 to 5 carbon atoms that is optionally interrupted by 1 or 2 —O—, —S— or —NR₆— radicals, and/or unsubstituted or substituted by =O or as R₁ and R₂ above in the meaning of alkyl, and/or condensed with benzene, pyridine, pyrimidine, furan, thiophene or pyrrole; or
  R₂ is as defined hereinbefore and R₁ and R₃ together are alkylene having from 2 to 5 carbon atoms that is optionally interrupted by 1 or 2 —O—, —S— or —NR₆— radicals, and/or unsubstituted or substituted by =O or as R₁ and R₂ above in the meaning of alkyl, and/or condensed with benzene, pyridine, pyrimidine, furan, thiophene or pyrrole.

The radicals R₁, R₂ and R₃ may contain one or more chirality centres.

R₁, R₂ and R₃ can be substituted in any desired positions by identical or different radicals, for example by from 1 to 5, preferably from 1 to 3, substituents.

Suitable substituents for R₁ and R₂ and R₃ are: $C_1$–$C_{12}$-, preferably $C_1$–$C_6$-, and especially $C_1$–$C_4$-alkyl, -alkoxy or -alkylthio, e.g. methyl, ethyl, propyl, n-, iso- and tert-butyl, the isomers of pentyl, hexyl, octyl, nonyl, decyl, undecyl and dodecyl, and corresponding alkoxy and alkylthio radicals;

$C_1$–$C_6$-, preferably $C_1$–$C_4$-haloalkyl having preferably F and Cl as halogen, e.g. trifluoro- or trichloro-methyl difluorochloromethyl, fluorodichloromethyl, 1,1-difluoroeth-1-yl, 1,1-dichloroeth-1-yl, 1,1,1-trichloro- or 1,1,1-trifluoroeth-2-yl, pentachloroethyl, pentafluoroethyl, 1,1,1-trifluoro-2,2-dichloroethyl, n-perfluoropropyl, iso-perfluoropropyl, n-perfluorobutyl, fluoro- or chloro-methyl, difluoro- or dichloro-methyl, 1-fluoro- or 1-chloro-eth-2-yl or -eth-1-yl, 1-, 2- or 3-fluoro- or 1-, 2- or 3-chloro-prop-1-yl or -prop-2-yl or -prop-3-yl, 1-fluoro- or 1-chloro-but-1-yl, -but-2-yl, -but-3-yl or -but-4-yl, 2,3-dichloroprop-1-yl, 1-chloro-2-fluoro-prop-3-yl, 2,3-dichlorobut-1-yl;

$C_6$–$C_{12}$-aryl, -aryloxy or -arylthio, in which aryl is preferably naphthyl and especially phenyl, $C_7$–$C_{16}$-aralkyl, -aralkoxy and -aralkylthio, in which the aryl radical is preferably naphthyl and especially phenyl and the alkylene radical is linear or branched and contains from 1 to 10, preferably from 1 to 6 and especially from 1 to 3, carbon atoms, for example benzyl, naphthylmethyl, 1- or 2-phenyl-eth-1-yl or -eth-2-yl, 1-, 2- or 3-phenyl-prop-1-yl, -prop-2-yl or -prop-3-yl, with benzyl being especially preferred;

the radicals containing the aryl groups mentioned above may in turn be mono- or poly-substituted, for example by $C_1$–$C_4$-alkyl, -alkoxy or -alkylthio, halogen, —OH, —CONR₄R₅ or by —COOR₅, wherein R₄ and R₅ are as defined; examples are methyl, ethyl, n- and isopropyl, butyl, corresponding alkoxy and alkylthio radicals, F, Cl, Br, dimethyl-, methyl- ethyl- and diethyl-carbamoyl and methoxy-, ethoxy-, phenoxy- and benzyloxy-carbonyl; halogen, preferably F and Cl; secondary amino having from 2 to 24, preferably from 2 to 12 and especially from 2 to 6 carbon atoms, the secondary amino preferably containing 2 alkyl groups, for example dimethyl-, methylethyl-, diethyl-, methylpropyl-, methyl-n-butyl-, di-n-propyl-, di-n-butyl-, di-n-hexyl-amino;

—CONR₄R₅, wherein R₄ and R₅ are each independently of the other $C_1$–$C_{12}$-, preferably $C_1$–$C_6$-, and especially $C_1$–$C_4$-alkyl, or R₄ and R₅ together are tetra- or penta-methylene or 3-oxapentylene, the alkyl being linear or branched, e.g. dimethyl-, methylethyl-, diethyl-, methyl-n-propyl-, ethyl-n-propyl-, di-n-propyl-, methyl-n-butyl-, ethyl-n-butyl-, n-propyl-n-butyl- and di-n-butyl-carbamoyl;

—COOR₄, wherein R₄ is $C_1$–$C_{12}$-, preferably $C_1$–$C_6$-alkyl, which may be linear or branched, e.g. methyl, ethyl, n- and iso-propyl, n-, iso- and tert-butyl, and the isomers of pentyl, hexyl, heptyl, octyl, nonyl decyl undecyl and dodecyl.

R₁, R₂ and R₃ may contain especially functional groups, such as keto groups, —CN, —NO₂, carbon double bonds, N—O—, aromatic halogen groups and amide groups.

R₁ and R₂ as heteroaryl are preferably a 5- or 6-membered ring having 1 or 2 identical or different hetero atoms, especially O, S or N, which contains preferably 4 or 5 carbon atoms and can be condensed with benzene. Examples of heteroaromatics from which R₁ can be derived are furan, pyrrole, thiophene, pyridine, pyrimidine, indole and quinoline.

R₁ and R₂ as heteroaryl-substituted alkyl are derived preferably from a 5- or 6-membered ring having 1 or 2 identical or different hetero atoms, especially O, S or N, which contains preferably 4 or 5 carbon atoms and can be condensed with benzene. Examples of heteroaromatics are furan, pyrrole, thiophene, pyridine, pyrimidine, indole and quinoline.

$R_1$ and $R_2$ as heterocycloalkyl or as heterocycloalkyl-substituted alkyl contain preferably from 4 to 6 ring atoms and 1 or 2 identical or different hetero atoms from the group O, S and $NR_6$. It can be condensed with benzene. It may be derived, for example, from pyrrolidine, tetrahydrofuran, tetrahydrothiophene, indane, pyrazolidine, oxazolidine, piperidine, piperazine or morpholine.

$R_1$, $R_2$ and $R_3$ as alkyl are preferably unsubstituted or substituted $C_1$–$C_6$-, especially $C_1$–$C_4$-alkyl, which may be linear or branched. Examples are methyl, ethyl, iso- and n-propyl, iso-, n- and tert-butyl, the isomers of pentyl, hexyl, heptyl, octyl, nonyl, decyl, undecyl and dodecyl.

$R_1$, $R_2$ and $R_3$ as unsubstituted or substituted cycloalkyl contain preferably from 3 to 6, especially 5 or 6, ring carbon atoms. Examples are cyclopropyl, cyclobutyl, cyclopentyl, cyclohexyl, cycloheptyl and cyclooctyl.

$R_1$, $R_2$ and $R_3$ as aryl are preferably unsubstituted or substituted naphthyl and especially phenyl. $R_1$, $R_2$ and $R_3$ as aralkyl are preferably unsubstituted or substituted phenylalkyl having from 1 to 10, preferably from 1 to 6 and especially from 1 to 4 carbon atoms in the alkylene, the alkylene being linear or branched. Examples are especially benzyl, and 1-phenyleth-1-yl, 2-phenyleth-1-yl, 1-phenylprop-1-yl, 1-phenylprop-2-yl, 1-phenylprop-3-yl, 2-phenylprop-1-yl, 2-phenylprop-2-yl and 1-phenylbut-4-yl.

In $R_2$ and $R_3$ as —$CONR_4R_5$ and —$COOR_4$, $R_4$ and $R_5$ are preferably $C_1$–$C_6$-, especially $C_1$–$C_4$-alkyl, or $R_4$ and $R_5$ together are tetramethylene, pentamethylene or 3-oxapentylene. Examples of alkyl are mentioned hereinbefore.

$R_1$ and $R_2$ together or $R_1$ and $R_3$ together as alkylene are preferably interrupted by 1 —O—, —S— or —$NR_6$—, preferably —O—. $R_1$ and $R_2$ together or $R_1$ and $R_3$ together form, with the carbon atom or with the —N=C group to which they are bonded, respectively, preferably a 5- or 6-membered ring. For the substituents the preferences mentioned hereinbefore apply. As condensed alkylene, $R_1$ and $R_2$ together or $R_1$ and $R_3$ together are preferably alkylene condensed with benzene or pyridine. Examples of alkylene are: ethylene, 1,2- or 1,3-propylene, 1,2-, 1,3- or 1,4-butylene, 1,5-pentylene and 1,6-hexylene. Examples of interrupted or =O-substituted alkylene are 2-oxa-1,3-propylene, 2-oxa-1,4-butylene, 2-oxa- or 3-oxa-1,5-pentylene, 3-thia-1,5-pentylene, 2-thia-1,4-butylene, 2-thia-1,3-propylene, 2-methylimino-1,3-propylene, 2-ethylimino-1,4-butylene, 2- or 3-methyl-imino-1,5-pentylene, 1-oxo-2-oxa-1,3-propylene, 1-oxo-2-oxa-1,4-butylene, 2-oxo-3-oxa-1,4-butylene, 1-oxa-2-oxo-1,5-pentylene. Examples of condensed alkylene are:

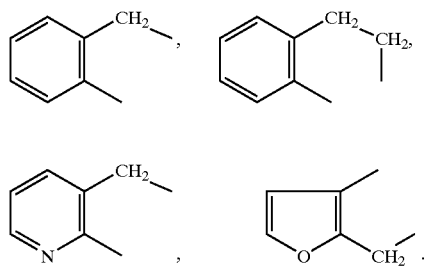

Examples of condensed and interrupted and unsubstituted or =O-substituted alkylene are:

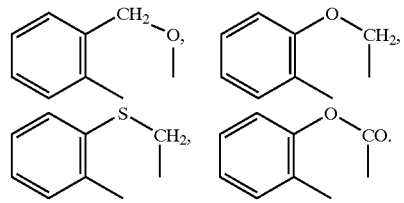

$R_4$ and $R_5$ are preferably each independently of the other hydrogen, $C_1$–$C_4$alkyl, phenyl or benzyl. $R_6$ is preferably hydrogen or $C_1$–$C_4$alkyl.

A further preferred group is formed by prochiral imines in which in formula I $R_1$, $R_2$ and $R_3$ are each different from the others and are not hydrogen.

In an especially preferred group, in formula I $R_3$ is 2,6-di-$C_1$–$C_4$alkylphen-1-yl and especially 2,6-dimethylphen-1-yl or 2-methyl-6-ethylphen-1-yl, $R_1$ is $C_1$–$C_4$alkyl and especially ethyl or methyl, and $R_2$ is $C_1$–$C_4$alkyl, $C_1$–$C_4$alkoxymethyl or $C_1$–$C_4$alkoxyethyl, and especially methoxymethyl.

Of those compounds, imines of formulae

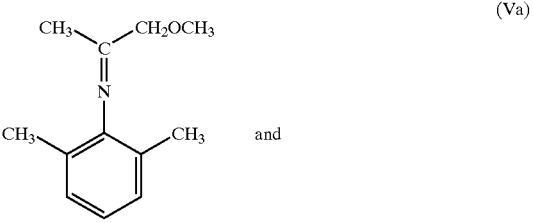

and

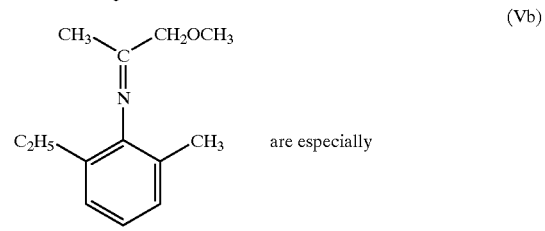

are especially important, as is the imine of the formula

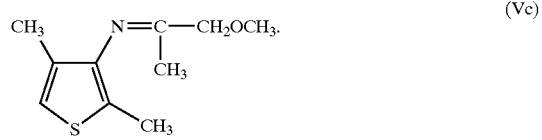

Imines of formula I are known or they can be prepared in accordance with known processes from aldehydes or ketones and primary amines.

The iridium catalysts are preferably homogeneous catalysts that are substantially soluble in the reaction medium. The term "catalyst" also includes catalyst precursors that are converted into an active catalyst species at the beginning of a hydrogenation. The catalysts preferably correspond to the formulae III, IIIa, IIIb, IIIc and IIId,

[XIrYZ]               (III),

[XIrY]$^\oplus$A$^\ominus$             (IIIa),

[YIrZ$_4$]$^\ominus$M$^\oplus$             (IIIb), $$[YIrHZ_2]_2 \quad (IIIc),$$

$$[YIrZ_3]_2 \quad (IIId),$$

wherein X is two olefin ligands or a diene ligand, Y is a ditertiary diphosphine
(a) the phosphine groups of which are bonded to different carbon atoms of a carbon chain having from 2 to 4 carbon atoms, or
(b) the phosphine groups of which are either bonded directly or via a bridge group —$CR_aR_b$— in the ortho positions of a cyclopentadienyl ring or are each bonded to a cyclopentadienyl ring of a ferrocenyl, or
(c) one phosphine group of which is bonded to a carbon chain having 2 or 3 carbon atoms and the other phosphine group of which is bonded to an oxygen atom or a nitrogen atom bonded terminally to that carbon chain, or
(d) the phosphine groups of which are bonded to the two oxygen atoms or nitrogen atoms bonded terminally to a $C_2$-carbon chain;
with the result that in the cases of (a), (b), (c) and (d) a 5-, 6- or 7-membered ring is formed together with the Ir atom, the radicals Z are each independently of the other(s) Cl, Br or I, $A^\ominus$ is the anion of an oxy or complex acid, and $M^\oplus$ is an metal cation or quaternary ammonium, and $R_a$ and $R_b$ are each independently of the other hydrogen, $C_1$–$C_8$alkyl, $C_1$–$C_4$fluoroalkyl, phenyl or benzyl or are phenyl or benzyl having from 1 to 3 $C_1$–$C_4$alkyl or $C_1$–$C_4$alkoxy substituents. $R_b$ is preferably hydrogen. $R_a$ is preferably $C_1$–$C_4$alkyl and especially methyl.

The diphosphine Y contains preferably at least one chiral carbon atom and is especially an optically pure stereoisomer (enantiomer or diastereoisomer), or a pair of diastereoisomers, since the use of catalysts containing those ligands leads to optical induction in asymmetric hydrogenation reactions.

X as an olefin ligand may be a branched or, preferably, linear $C_2$–$C_{12}$alkylene, especially $C_2$–$C_6$alkylene. Some examples are dodecylene, decylene, octylene, 1-, 2- or 3-hexene, 1-, 2- or 3-pentene, 1- or 2-butene, propene and ethene. X as a diene ligand may be open-chain or cyclic dienes having from 4 to 12, preferably from 5 to 8, carbon atoms, the diene groups preferably being separated by one or two saturated carbon atoms. Some examples are butadiene, pentadiene, hexadiene, heptadiene, octadiene, decadiene, dodecadiene, cyclopentadiene, cyclohexadiene, cycloheptadiene, cyclooctadiene and bridged cyclodienes such as norbornadiene and bicyclo-2,2,2-octadiene. Hexadiene, cyclooctadiene and norbornadiene are preferred.

The phosphine groups contain preferably two identical or different, preferably identical, unsubstituted or substituted hydrocarbon radicals having from 1 to 20, especially from 1 to 12 carbon atoms. Preference is given to diphosphines wherein the secondary phosphine groups contain two identical or different radicals from the following group: linear or branched $C_1$–$C_{12}$alkyl; unsubstituted or $C_1$–$C_6$alkyl- or $C_1$–$C_6$alkoxy-substituted $C_5$–$C_{12}$-cycloalkyl, $C_5$–$C_{12}$cycloalkyl-$CH_2$-, phenyl or benzyl; and phenyl or benzyl substituted by halogen (e.g. F, Cl or Br), $C_1$–$C_6$haloalkyl, $(C_1$–$C_{12}$alkyl$)_3$Si, $(C_6H_5)_3$Si, $C_1$–$C_6$haloalkoxy (e.g. trifluoromethoxy), —$NH_2$, phenyl$_2$N—, benzyl$_2$N—, morpholinyl, piperidinyl pyrrolidinyl, $(C_1$–$C_{12}$alkyl$)_2$N—, -ammonium-$X_1^\ominus$, —$SO_3M_1$, —$CO_2M_1$, —$PO_3M_1$ or by —COO—$C_1$–$C_6$alkyl (e.g. —$COOCH_3$), wherein $M_1$ is an alkali metal or hydrogen and $X_1^\ominus$ is the anion of a monobasic acid. $M_1$ is preferably H, Li, Na or K. $A_1^\ominus$, as the anion of a monobasic acid, is preferably $Cl^\ominus$, $Br^\ominus$ or the anion of a carboxylic acid, for example formate, acetate, trichloroacetate or trifluoroacetate.

A secondary phosphine group may also be a radical of the formula

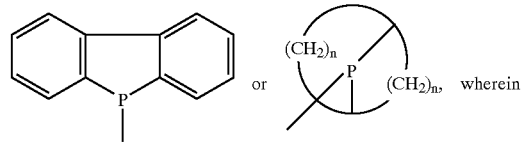

m and n are each independently of the other an integer from 2 to 10, and the sum of m+n is from 4 to 12, especially from 5 to 8. Examples thereof are [3.3.1]- and [4.2.1]-phobyl of the formulae

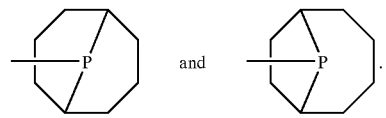

Examples of alkyl that preferably contains from 1 to 6 carbon atoms are methyl, ethyl, n-propyl, isopropyl, n-, iso- and tert-butyl and the isomers of pentyl and hexyl. Examples of unsubstituted or alkyl-substituted cycloalkyl are cyclopentyl, cyclohexyl, methyl- or ethyl-cyclohexyl and dimethylcyclohexyl. Examples of alkyl-, alkoxy- or haloalkoxy-substituted phenyl and benzyl are methylphenyl, dimethylphenyl trimethylphenyl, ethylphenyl, methylbenzyl methoxyphenyl dimethoxyphenyl, trfluoromethylphenyl, bis-trifluoromethylphenyl tris-trifluoromethylphenyl, trifluoromethoxyphenyl and bis-trifluoromethoxyphenyl. Preferred phosphine groups are those that contain identical or different, preferably identical, radicals from the group $C_1$–$C_6$alkyl; cyclopentyl and cyclohexyl that are unsubstituted or have from 1 to 3 $C_1$–$C_4$alkyl or $C_1$–$C_4$alkoxy substituents, benzyl and, especially, phenyl that is unsubstituted or has from 1 to 3 $C_1$–$C_4$alkyl, $C_1$–$C_4$alkoxy, F, Cl, $C_1$–$C_4$fluoroalkyl or $C_1$–$C_4$fluoroalkoxy substituents.

Y as a diphosphine is preferably of formula IV, IVa, IVb, IVc or IVd,

 (IV),

 (IVa),

 (IVb),

 (IVc),

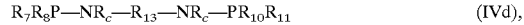 (IVd), wherein
$R_7$, $R_8$, $R_{10}$ and $R_{11}$ are each independently of the others a hydrocarbon radical having from 1 to 20 carbon atoms that is unsubstituted or substituted by $C_1$–$C_6$alkyl, $C_1$–$C_6$alkoxy, halogen, $C_1$–$C_6$haloalkyl, $(C_1$–$C_{12}$alkyl$)_3$Si, $(C_6H_5)_3$Si, $C_1$–$C_6$haloalkoxy, —$NH_2$, phenyl$_2$N—, benzyl$_2$N—, morpholinyl, piperidinyl, pyrrolidinyl $(C_1$–$C_{12}$alkyl$)_2$N—, -ammonium-$X_1^\ominus$, —$SO_3M_1$, —$CO_2M_1$, —$PO_3M_1$ or by —COO—$C_1$–$C_6$alkyl, wherein $M_1$ is an alkali metal or hydrogen and $X_1^\ominus$ is the anion of a monobasic acid;
$R_9$ is linear $C_2$–$C_4$alkylene that is unsubstituted or substituted by $C_1$–$C_6$alkyl, $C_5$- or $C_6$-cycloalkyl, phenyl, naphthyl or by benzyl; 1,2- or 1,3-cycloalkylene or -cycloalkenylene, -bicycloalkylene or -bicycloalkenylene having from 4 to 10 carbon atoms, each of which is unsubstituted or substituted by $C_1-C_6$alkyl, phenyl or by benzyl; 1,2- or 1,3-cycloalkylene or -cycloalkenylene, -bicycloalkylene or -bicycloalkenylene having from 4 to 10 carbon atoms, each of which is unsubstituted or substituted by $C_1-C_6$alkyl, phenyl or by benzyl, and in the 1- and/or 2-positions or in the 3-position of which methylene or $C_2-C_4$alkylidene is bonded; 1,4-butylene substituted in the 2,3-positions by

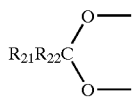

and unsubstituted or substituted in the 1,4-positions by $C_1-C_6$alkyl, phenyl or by benzyl, wherein $R_{21}$ and $R_{22}$ are each independently of the other hydrogen, $C_1-C_6$alkyl, phenyl or benzyl; 3,4- or 2,4-pyrrolidinylene or 2-methylene-pyrrolidin-4-yl the nitrogen atom of which is substituted by hydrogen, $C_1-C_{12}$alkyl, phenyl, benzyl, $C_1-C_{12}$alkoxycarbonyl, $C_1-C_8$acyl or by $C_1-C_{12}$alkylaminocarbonyl; or 1,2-phenylene, 2-benzylene, 1,2-xylylene, 1,8-naphthylene, 2,2'-dinaphthylene or 2,2'-diphenylene, each of which is unsubstituted or substituted by $C_1-C_4$alkyl;

or $R_9$ is a radical of the formula

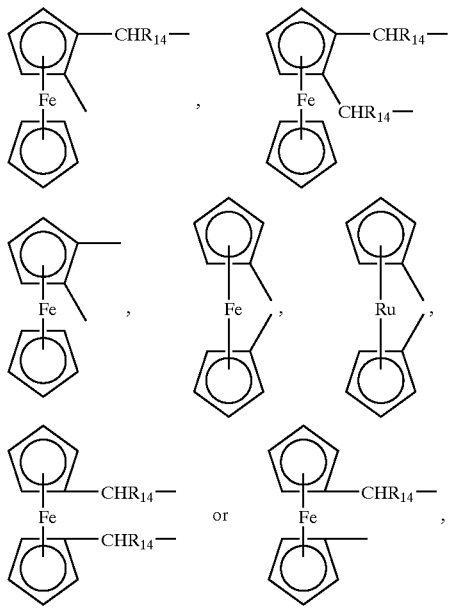

wherein $R_{14}$ is hydrogen, $C_1-C_8$alkyl, $C_1-C_4$fluoroalkyl, phenyl or phenyl having from 1 to 3 $C_1-C_4$alkyl or $C_1-C_4$alkoxy substituents;

$R_{12}$ is linear $C_2$- or $C_3$-alkylene that is unsubstituted or substituted by $C_1-C_6$alkyl, $C_5$- or $C_6$-cycloalkyl, phenyl, naphthyl or by benzyl; 1,2- or 1,3-cycloalkylene or -cycloalkenylene, -bicycloalkylene or -bicycloalkenylene having from 4 to 10 carbon atom, each of which is unsubstituted or substituted by $C_1-C_6$alkyl, phenyl or by benzyl; or 1,2- or 1,3-cycloalkylene or -cycloalkenylene, -bicycloalkylene or -bicycloalkenylene having from 4 to 10 carbon atoms, each of which is unsubstituted or substituted by $C_1-C_6$alkyl, phenyl or by benzyl, and in the 1- and/or 2-positions or in the 3-position of which methylene or $C_2-C_4$alkylidene is bonded; 3,4- or 2,4-pyrrolidinylene or 3-methylene-pyrrolidin-4-yl the nitrogen atom of which is substituted by hydrogen, $C_1-C_{12}$alkyl, phenyl, benzyl, $C_1-C_{12}$alkoxycarbonyl, $C_1-C_8$acyl or by $C_1-C_{12}$alkylaminocarbonyl; or 1,2-phenylene, 2-benzylene, 1,2-, 2,3- or 1,8-naphthylene, each of which is unsubstituted or substituted by $C_1-C_4$alkyl; and $R_{13}$ is linear $C_2$-alkylene that is unsubstituted or substituted by $C_1-C_6$alkyl, $C_5$- or $C_6$-cycloalkyl, phenyl, naphthyl or by benzyl; 1,2-cycloalkylene or -cycloalkenylene, -bicycloalkylene or -bicycloalkenylene having from 4 to 10 carbon atoms, each of which is unsubstituted or substituted by $C_1-C_6$alkyl, phenyl or by benzyl; 3,4-pyrrolidinylene the nitrogen atom of which is substituted by hydrogen, $C_1-C_{12}$alkyl, phenyl, benzyl, $C_1-C_{12}$alkoxycarbonyl, $C_1-C_8$acyl or by $C_1-C_{12}$alkylaminocarbonyl; or 1,2-phenylene that is unsubstituted or substituted by $C_1-C_4$alkyl, or is a radical, less two hydroxy groups in the ortho positions, of a mono- or di-saccharide, and $R_c$ is hydrogen, $C_1-C_4$alkyl, phenyl or benzyl.

$R_7$, $R_8$, $R_{10}$ and $R_{11}$ are preferably identical or different, preferably identical, radicals from the following group: $C_1-C_6$alkyl; cyclopentyl and cyclohexyl that are unsubstituted or have from 1 to 3 $C_1-C_4$alkyl or $C_1-C_4$alkoxy substituents, benzyl and, especially, phenyl that is unsubstituted or has from 1 to 3 $C_1-C_4$alkyl, $C_1-C_4$alkoxy, F, Cl, $C_1-C_4$fluoroalkyl or $C_1-C_4$fluoroalkoxy substituents.

A preferred subgroup of diphosphines Y is formed by those of the formulae

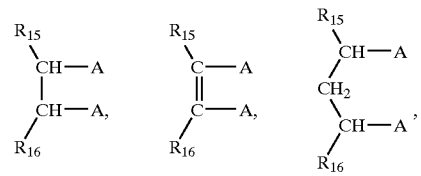

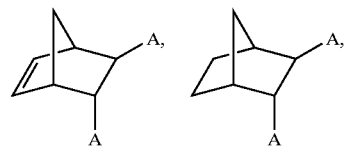

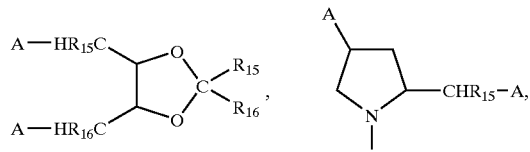

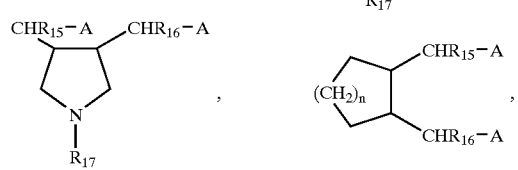

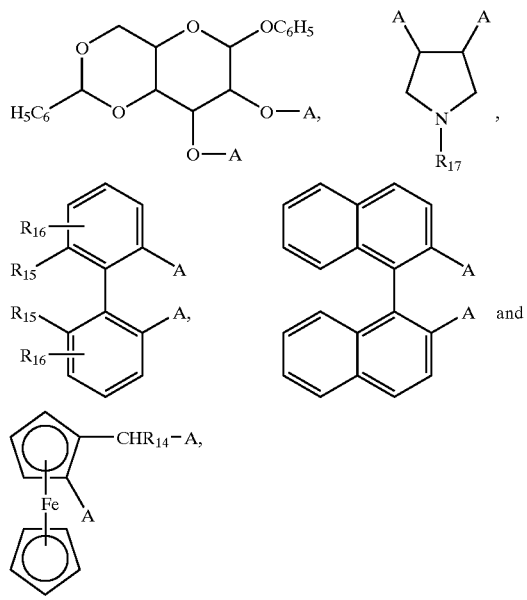

wherein $R_{15}$ and $R_{16}$ are each independently of the other hydrogen, $C_1$–$C_4$alkyl, phenyl, benzyl, or phenyl or benzyl having from 1 to 3 $C_1$–$C_4$alkyl or $C_1$–$C_4$alkoxy substituents, $R_{14}$ is hydrogen, $C_1$–$C_4$alkyl, phenyl, benzyl, or phenyl or benzyl having from 1 to 3 $C_1$–$C_4$alkyl or $C_1$–$C_4$alkoxy substituents, $R_{17}$ is hydrogen, $C_1$–$C_4$alkyl, phenyl, benzyl $C_1$–$C_6$alkoxy-CO—, $C_1$–$C_6$alkyl-CO—, phenyl-CO—, naphthyl-CO— or $C_1$–$C_4$alkylNH—CO—, A may be identical or different groups —$PR_2$, wherein R is $C_1$–$C_6$alkyl, cyclohexyl, phenyl, benzyl, or phenyl or benzyl having from 1 to 3 $C_1$–$C_4$alkyl, $C_1$–$C_4$alkoxy, —$CF_3$ or partially or fully fluorinated $C_1$–$C_4$alkoxy substituents, and n is 0, 1 or 2.

Of those diphosphines, chirally substituted compounds are especially preferred.

Some preferred examples of diphosphines Y are as follows (Ph is phenyl):

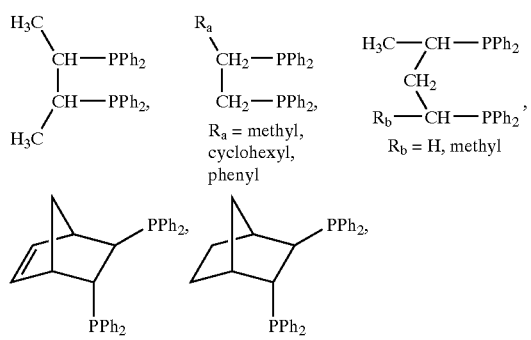

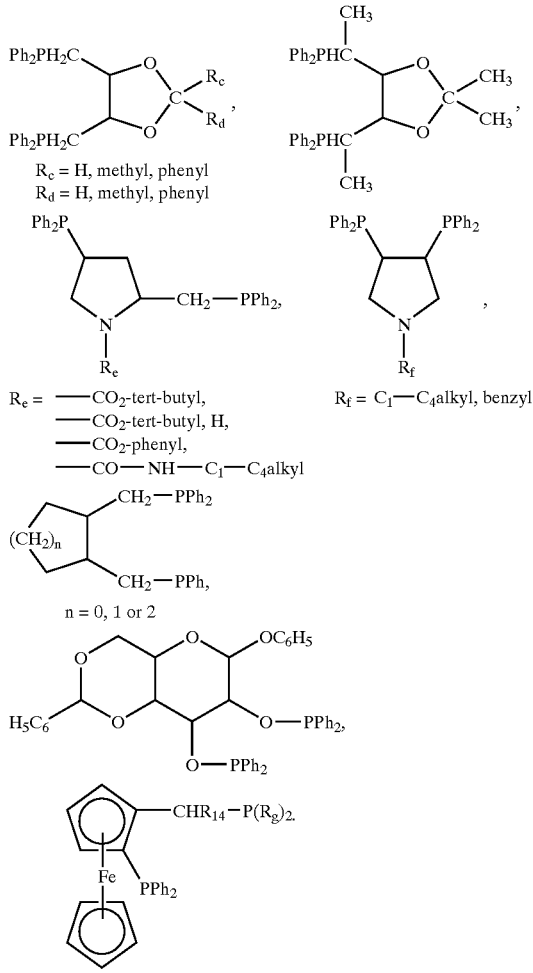

Suitable diphosphines and diphosphinites have been described, for example, by H. B. Kagan in Chiral Ligands for Asymmetric Catalysis, Asymmetric Synthesis, Volume 5, pp. 13–23. Academic Press, Inc., N.Y. (1985). The preparation of ferrocenyl diphosphine ligands is described, for example, in EP-A0 564 406 and by T. Hayashi et al. in Bull. Chem. Soc. Jpn., 53, pages 1136–1151.

$A^{\ominus}$ in formula IIIa can be derived from inorganic or organic oxy acids. Examples of such acids are $H_2SO_4$, $HClO_4$, $HClO3$, $HBrO_4$, $HIO_4$, $HNO_3$, $H_3PO_3$, $H_3PO_4$, $CF_3SO_3H$, $C_6H_5SO_3H$, $CF_3COOH$ and $CCl_3COOH$. Complex acids from which $A^{\ominus}$ can be derived are, for example, the halo complex acids of the elements B, P, As, Sb and Bi. Preferred examples of $A^{\ominus}$ in formula IIIa are $ClO_4^{\ominus}$, $CF_3SO_3^{\ominus}$, $BF_4^{\ominus}$, $B(phenyl)_4^{\ominus}$, $PF_6^{\ominus}$, $SbCl_6^{\ominus}$, $AsF_6^{\ominus}$ and $SbF_6^{\ominus}$.

When $M^{\oplus}$ in formula IIIb is an alkali metal cation, it may be, for example, a Li, Na, K, Rb or Cs cation. When $M^{\oplus}$ is quaternary ammonium, it may contain a total of from 4 to 40, preferably from 4 to 24, carbon atoms. $M^{\oplus}$ may correspond to the formula phenyl-$N^{\oplus}(C_1$–$C_6alkyl)_3$, benzyl$N^{\oplus}(C_1$–$C_6alkyl)_3$ or $(C_1$–$C_6alkyl)_4N^{\oplus}$. $M^{\oplus}$ in formula IIIb is preferably $Li^{\oplus}$, $Na^{\oplus}$ or $K^{\oplus}$ or $(C_1$–$C_6alkyl)_4N^{\oplus}$.

Z in formula III is preferably Br or Cl and especially Cl. Z in formula IIIb is preferably Br or I and Z in formulae IIIc and IIId is preferably I.

Especially suitable diphosphine ligands which can preferably be used in catalysts of formula (III) are, for example:

{(R)-1-[(S)-2-diphenylphosphino)ferrocenyl]}ethyl-di(3,
5-dimethyl-4-N,N-dipropylaminophenyl)phosphine {(R)-1-[(S)-2-diphenylphosphino)ferrocenyl]}ethyl-di(3,
5-diisopropyl-4-N,N-dimethylaminophenyl)phosphine {(R)-1-[(S)-2-diphenylphosphino)ferrocenyl]}ethyl-di(3,
5-diisopropyl-4-N,N-dibenzylylaminophenyl)phosphine {(R)-1-[(S)-2-diphenylphosphino)ferrocenyl]}ethyl-di(3,
5-dimethyl-4-N,N-dibenzylylaminophenyl)phosphine {(R)-1-[(S)-2-diphenylphosphino)ferrocenyl]}ethyl-di(3,
5-dimethyl-4-(1'-pyrrolo)phenyl)phosphine {(R)-1-[(S)-2-diphenylphosphino)ferrocenyl]}ethyl-di(3,
5-dimethyl-4-N,N-dipentylaminophenyl)phosphine {(R)-1-[(S)-2-diphenylphosphino)ferrocenyl]}ethyl-di(3,
5-dimethyl-4-N,N-dimethylaminophenyl)phosphine 1,4-bis(diphenylphosphino)butane {(R)-1-[(S)-2-di(4-methoxyphenyl)phosphino)
ferrocenyl]}ethyl-di(3,5-dimethyl-4-N,N-
dimethylaminophenyl)phosphine and preferably {(R)-1-[(S)-2-diphenylphosphino)ferrocenyl]}ethyl-di(3,
5-dimethyl-phenyl)phosphine.

The preparation of the catalysts is known per se and is described, for example, in U.S. Pat. No. 4,994,615, U.S. Pat. No. 5,011,995, U.S. Pat. No. 5,112,999 and EP-A-0 564 406. The preparation of the catalysts of formula III can be carried out, for example, by reacting a diiridium complex of the formula [IrXZ]$_2$ with a diphosphine Y. The iridium catalysts can be added to the reaction mixture as isolated compounds. It has proved advantageous, however, to produce the catalyst in situ with or without a solvent prior to the reaction and to add optionally a portion or all of the acid and of an ammonium or alkali metal halide.

The iridium catalysts are preferably used in amounts of from 0.0001 to 10 mol %, especially from 0.001 to 10 mol %, and more especially from 0.01 to 5 mol %, based on the imine.

The molar ratio of the imine to the iridium catalyst may be, for example, from 5 000 000 to 10, especially from 2 000 000 to 20, more preferably from 1 000 000 to 20, and more especially from 500 000 to 100.

The process is carried out preferably at a temperature of from −20 to 100° C., especially from 0 to 80° C. and more especially from 10 to 70° C., and preferably at a hydrogen pressure of 2×10$^5$ to 1.5×10$^7$ Pa (5 to 150 bar), especially 10$^6$ to 10$^7$ Pa (10 to 100 bar).

The chorides, bromides and iodides employed are preferably used in concentrations of from 0.01 to 500 mmol/l, especially from 0.01 to 50 mmol/l, based on the volume of the reaction mixture.

The process according to the invention comprises the additional concomitant use of an ammonium or metal chloride, bromide or iodide. The chlorides, bromides and iodides are used preferably in amounts of from 0.01 to 200 mol %, especially from 0.05 to 100 mol % and more especially from 0.5 to 50 mol %, based on the iridium catalyst. The iodides are preferred. Ammonium is preferably tetraalkylammonium having from 1 to 6 carbon atoms in the alkyl groups, and the metal is preferably sodium, lithium or potassium. Special preference is given to tetrabutylammonium iodide and sodium.

Provided that they are soluble in the reaction mixture and provided that oxidation reactions with other reactants can be ruled out, virtually any metal chlorides, bromides and iodides, that is to say those of the main groups and subgroups of the Periodic Table of the Elements, can be used in the process according to the invention.

The reaction can be carried out in the absence or in the presence of solvents. Suitable solvents, which can be used alone or as a mixture of solvents, are especially aprotic solvents. Examples are:

aliphatic and aromatic hydrocarbons, such as pentane, hexane, cyclohexane, methylcyclohexane, benzene, toluene and xylene; ethers, such as diethyl ether, diethylene glycol dimethyl ether, tetrahydrofuran and dioxane; halogenated hydrocarbons, such as methylene chloride, chloroform, 1,1,2,2-tetrachloroethane and chlorobenzene; esters and lactones, such as ethyl acetate, butyrolactone and valerolactone; acid amides and lactams, such as dimethylformamide, dimethylacetamide and N-methylpyrrolidone, and ketones, such as acetone, dibutyl ketone, methyl isobutyl ketone and methoxyacetone.

The process according to the invention further comprises the additional concomitant use of an acid. It may be an inorganic or, preferably, an organic acid. The acid is preferably used in at least the same molar amount as the iridium catalyst (equivalent to catalytic amounts) and can also be used in excess. The excess may even consist in the use of the acid as solvent. Preferably from 0.001 to 50, in particular from 0.1 to 50% by weight of acid is used, based on the amine. In many cases it can be advantageous to use anhydrous acids.

Some examples of inorganic acids are $H_2SO_4$, highly concentrated sulfuric acid (oleum), $H_3PO_4$, orthophosphoric acid, HF, HCl, HBr, HI, $HClO_4$, $HBF_4$, $HPF_6$, $HAsF_6$, $HSbCl_6$, $HSbF_6$ and $HB(phenyl)_4$. $H_2SO4$ is particularly preferred.

Examples of organic acids are aliphatic or aromatic, optionally halogenated (fluorinated or chlorinated) carboxylic acids, sulfonic acids, phosphorus(V) acids (for example phosphonic acids, phosphonous acids) having preferably from 1 to 20, especially from 1 to 12 and more especially from 1 to 6, carbon atoms. Examples are formic acid, acetic acid, propionic acid, butyric acid, benzoic acid, phenylacetic acid, cyclohexanecarboxylic acid, chloro- or fluoroacetic acid, dichloro- or difluoro-acetic acid, trichloro- or trifluoroacetic acid, chlorobenzoic acid, methanesulfonic acid, ethanesulfonic acid, benzenesulfonic acid, p-toluenesulfonic acid, chlorobenzenesulfonic acid, trifluoromethanesulfonic acid, methylphosphonic acid and phenylphosphonic acid. Preferred acids are acetic acid, propionic acid, trifluoroacetic acid, methanesulfonic acid and chloroacetic acid.

It is also possible for acidic ion exchangers of an inorganic or organic nature to be used as the acids.

In detail, the process according to the invention can be carried out by first preparing the catalyst by dissolving, for example, (Ir-dieneCl)$_2$ in a solvent or an acid or both, adding a diphosphine and then an alkali metal or ammonium halide and stirring the mixture. (Ir-dieneCl)$_2$ can also be used in solid form. A solution of imines is added to that catalyst solution (or vice versa) and, in an autoclave, hydrogen pressure is applied, thus removing the protective gas that is advantageously used. It is advantageous to ensure that the catalyst solution stands for only a short time, and to carry out the hydrogenation of the imines as soon as possible after the preparation of the catalyst. The reaction mixture is heated, if desired, and then hydrogenated. Where appropriate, when the reaction has ceased the reaction mixture is cooled and the autoclave is depressurised. The reaction mixture can be removed from the autoclave under pressure with nitrogen and the hydrogenated organic compound can be isolated and purified in a manner known per se, for example by precipitation, extraction or distillation.

In the case of the hydrogenation of aldimines and ketimines, the aldimines and ketimines can also be formed in situ before or during the hydrogenation. In a preferred form, an amine and an aldehyde or a ketone are mixed together and added to the catalyst solution and the aldimine or ketimine formed in situ is hydrogenated. It is also possible, however, to use an amine, a ketone or an aldehyde together with the catalyst as the initial batch and to add the ketone or the aldehyde or the amine thereto, either all at once or in metered amounts.

The hydrogenation can be carried out continuously or batchwise in various types of reactor. Preference is given to those rectors which allow comparatively good intermixing and good removal of heat, such as, for example, loop reactors. That type of reactor has proved to be especially satisfactory when small amounts of catalyst are used.

The process according to the invention yields the corresponding amines in short reaction times while having chemically a high degree of conversion, with surprisingly good optical yields (ee) of 70% or more being obtained even at relatively high temperatures of more than 50° C., and even with high molar ratios of imine to catalyst.

The hydrogenated organic compounds that can be prepared in accordance with the invention, for example the amines, are biologically active substances or are intermediates for the preparation of such substances, especially in the field of the preparation of pharmaceuticals and agrochemicals. For example, o,o-dialkylarylketamine derivatives, especially those having alkyl and/or alkoxyalkyl groups, are effective as fungicides, especially as herbicides. The derivatives may be amine salts, acid amides, for example of chloroacetic acid, tertiary amines and ammonium salts (see, for example, EP-A-0 077,755 and EP-A-0 115 470).

Especially important in this connection are the optically active amines of formula

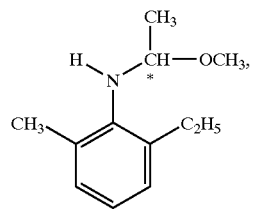

(VI)

which can be prepared from the imines of formula (V) using the processes according to the invention, wherein $R_{01}$, $R_{02}$ and $R_{03}$ are each independently of the others $C_1$–$C_4$alkyl, and $R_{04}$ is $C_1$–$C_4$alkyl or $C_1$–$C_4$alkoxymethyl or $C_1$–$C_4$alkoxyethyl, and especially the amines of the formulae

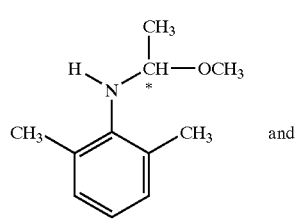

(VIa)

and

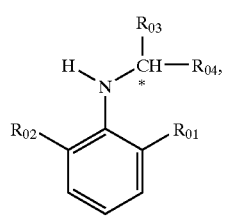

(VIb)

which can be prepared from the imines of the formulae (Va) and (Vb) and which can be converted in accordance with methods that are customary per se with chloroacetic acid into the desired herbicides of the chloroacetanilide type.

The Examples that follow illustrate the invention in more detail. The chemical conversion is determined by gas chromatography [DB 17/30 W column (15 m), manufacturer: JCW Scientific Inc. USA, temperature programme: from 60° C./1 min to 220° C., ΔT: $10° \times min^{-1}$]. The optical yields (enantiomeric excess, ee) are determined either by gas chromatography [Chirasil-Val column, 50 m, manufacturer: Alltech, USA, T=150° C., isothermic], by HPLC (Chiracel OD column) or by $^1$H-NMR spectroscopy (using shift reagents).

EXAMPLE 1

Preparation of N-(2'-methyl-6'-ethyl-phen-1'-yl)-N-(1-methoxymethyl)ethylamine 17.2 mg (0.027 mmol) of {(R)-1-[(S)-2-diphenylphosphino)ferrocenyl]}ethyl-di(3,5dimethylphenyl)phosphine and 40 mg (0.108 mmol) of tetrabutylammonium iodide are introduced in succession into a solution of 8.8 mg (0.013 mmol) of [Ir(1,5-cyclooctadiene)Cl]$_2$ in 10 ml of acetic acid (degassed) and stirred for 15 minutes. Separately, 412 g (2 mol) of N-(2'-methyl-6'-ethyl-phen-1'-yl)-N-(1-methoxymethyl)eth-1-ylideneamine are dissolved in 70 ml of acetic acid (degassed). The imine solution and the catalyst solution are transferred in succession to a 1000 ml steel autoclave which is under an inert gas. In four cycles (10 bar, normal pressure) the inert gas is displaced by hydrogen. Then a pressure of 80 bar of hydrogen is applied and the autoclave heated to 50° C. After a reaction time of 18 hours, the reaction is discontinued and the reaction solution is cooled to room temperature. The hydrogen is depressurised and the reaction solution is expelled under pressure from the autoclave. The conversion is 100%. 100 ml of toluene are added and then toluene and acetic acid are removed in a rotary evaporator. The residue is distilled under a high vacuum (0.1 mbar), yielding 401 g (yield of 97%) of pure N-(2'-methyl-6'-ethyl-phen-1'-yl)-N-(1-methoxymethyl)ethylamine. A sample (2 g) is purified by means of flash chromatography [silica gel 0.040–0.063 mm, eluant hexane/ethyl acetate 10:1)] in order to determine the enantiomeric purity. The optical yield is 75.6% (S).

EXAMPLE 2

Preparation of N-(2'-methyl-6'-ethyl-phen-1'-yl)-N-(1-methoxymethyl)ethylamine 10.4 mg (0.0155 mmol) of [Ir(1,5-cyclooctadiene)Cl]$_2$, 21.4 mg (0.0335 mmol) of {(R)-1-[(S)-2-diphenylphosphino)ferrocenyl]}ethyl-di(3,5-dimethylphenyl)phosphine and 50 mg (0.136 mmol) of tetrabutylammonium iodide are dissolved in 2.5 ml of degassed acetic acid and stirred for 15 minutes. Separately, 17 g (0.083 mol) of 2-methyl-6-ethylaniline are dissolved in 9 g of anhydrous methoxyacetone. The methoxyacetone solution and the catalyst solution are transferred in succession to a 50 ml steel autoclave which is under an inert gas. In four cycles (10 bar, normal pressure) the inert gas is displaced by hydrogen. Then a pressure of 40 bar of hydrogen is applied and the autoclave is heated to 50° C. After a reaction time of 18 hours, the reaction is discontinued and the reaction solution is cooled to room temperature. Working up is effected in accordance with Example 1. The conversion is 97% (based on 2-methyl-6-ethylaniline) and the optical yield is 75.6% (S).

EXAMPLE 3

Preparation of N-(2'-methyl-6'-ethyl-phen-1'-yl)-N-(1-methoxymethyl)ethylamine 14.0 mg (0.032 mmol) of (2S,4S)-bis(diphenylphosphino)pentane (BDPP), 70 mg (0.19 mmol) of tetrabutylammonium iodide and 0.3 ml of methanesulfonic acid are introduced in succession into a solution of 10.2 mg (0.015 mmol) of [Ir(1,5-cyclooctadiene)-Cl]$_2$ in 3.5 ml of toluene (degassed) and stirred for 5 minutes. Separately, 3.12 g (15.2 mmol) of N-(2'-methyl-6'-ethyl-phen-1'-yl)-N-(1-methoxymethyl)eth-1-ylideneamine are dissolved in 3.2 ml of toluene (degassed). With the aid of a steel capillary the imine solution and the catalyst solution are transferred in succession to a 50 ml steel autoclave which is under an inert gas. In four cycles (10 bar, normal pressure) the inert gas is displaced by hydrogen. Then a pressure of 30 bars of hydrogen is applied. After a reaction period of 2.5 hours at 25° C. the reaction is discontinued. Working up is effected in accordance with Example 1. Conversion is 100% and the optical yield is 53.5% (R).

EXAMPLE 4

Preparation of N-(2'-methyl-6'-ethyl-phen-1'-yl)-N-(1-methoxymethyl)ethylamine

The process is carried out analogously to Example 3 and the reaction conditions are modified as follows:

0.35 ml of trifluoroacetic acid (instead of methanesulfonic acid). The reaction time is 2 hours, the conversion is 95% and the optical yield is 52.6% (R).

EXAMPLE 5

Preparation of N-(2'-methyl-6'-ethyl-phen-1'-yl)-N-(1-methoxymethyl)ethylamine

The process is carried out analogously to Example 3 and the reaction conditions are modified as follows:

0.4 g of ortho-phosphoric acid (instead of methanesulfonic acid) and 6.6 ml of tetrahydrofuran as solvent. The reaction time is 2.5 hours, the conversion is 98% and the optical yield is 53.4% (R).

EXAMPLE 6

Preparation of N-(2',4'-dimethylthiophen-3'-yl)-N-(1-methoxymethyl)ethylamine 8.6 mg (0.0125 mmol) of [Ir(1,5-cyclooctadiene)Cl]$_2$, 17.2 mg (0.0268 mmol) of {(R)-1-[(S)-2-diphenylphosphino)ferrocenyl]}ethyl-di(3,5-dimethylphenyl)phosphine (ligand) and 30 mg (0.08 mmol) of tetrabutylammonium iodide are introduced in succession into a 10 ml Schlenk flask which is under an argon atmosphere. 1 g (5 mmol) of N-(2',4'-dimethylthiophen-3'-yl)-N-(1-methoxymethyl)ethylideneamine, 5 ml of toluene and 2 ml of acetic acid are added thereto. That solution is transferred by means of a steel capillary to a 50 ml steel autoclave which is under argon. Then a pressure of 30 bar of hydrogen is applied as described in Example 1 and then the reaction solution is stirred for 20 minutes at room temperature. The reaction is discontinued, the hydrogen is depressurised and the reaction solution is expelled under pressure from the autoclave. Conversion is 100%. The solvent (toluene) and acid additive (acetic acid) are removed in a rotary evaporator, yielding 1.2 g of oily crude product, which is then purified by flash chromatography (silica gel 0.040–0.063 mm, eluant hexane/ethyl acetate (3:1)). The enantiomeric purity of the isolated product is 76.1%.

EXAMPLE 7

Preparation of N-(2',4'-dimethylthiophen-3'-yl)-N-(1-methoxymethyl)ethylamine

The process is carried out as in Example 6, but the reaction conditions are modified as follows:

ligand: 12.3 mg (0.028 mmol) of (2S,4S)-bis(diphenylphosphino)pentane, 55 mg (0.149 mmol) of tetrabutylammonium iodide. The reaction time is 1.4 hours. The conversion is complete, the ee is 47.5%.

EXAMPLE 8

Preparation of N-benzyl-N-(1-phenylethyl)amine

The process is carried out as in Example 6, but the reaction conditions are modified as follows: 0.636 g (3 mmol) of N-benzyl-N-(1-phenylethylidene)amine, 10.2 mg (0.0152 mmol) of [Ir(1,5-cyclooctadiene)Cl]$_2$, 21.4 mg (0.0333 mmol) of {(R)-1-[(S)-2-diphenylphosphino)ferrocenyl]}ethyl-di(3,5-dimethylphenyl)phosphine (ligand) and 15 mg (0.04 mmol) of tetrabutylammonium iodide, 2 ml of acetic acid, 15 ml of toluene, 30 bar of hydrogen, reaction temperature: 25° C. The reaction time is 20 minutes. The conversion is complete, the ee 31%.

EXAMPLE 9

Preparation of N-(2'-methyl-6'-ethyl-phen-1'-yl)-N-(1-methoxymethyl)ethylamine 2.7 mg (0.004 mmol) of [Ir(1,5-cyclooctadiene)Cl]$_2$ and 5.8 mg (0.009 mmol) of {(R)-1-[(S)-2-diphenylphosphino)ferrocenyl]}ethyl-di(3,5-dimethylphenyl)phosphine are weighed into a Schlenk flask, and then the Schlenk flask is placed under an argon atmosphere. Using a syringe, 2 ml of degassed tetrahydrofuran are then added and the orange solution is stirred for 30 minutes. 210 g (2 mol) of high-purity MEA-imine (>99%) of formula (Vb), 300 mg (0.8 mmol) of tetrabutylammonium iodide and 200 ml of acetic acid are introduced into a 1 liter laboratory autoclave. Then, using a syringe, 0.5 ml of the above catalyst solution is added. The ratio of imine/Ir is 1 000 000. The autoclave is closed and flushed first with nitrogen, then with hydrogen. Then a pressure of 80 bar of hydrogen is applied and the reaction solution is stirred for 65 hours at a temperature of 50° C. internal temperature. When the absorption of hydrogen is complete, the hydrogen is depressurised and then the reaction solution is analysed. The conversion is 100%, the enantioselectivity 75% ee (S).

EXAMPLES 10–22

Preparation of N-(2'-methyl-6'-ethyl-phen-1'-yl)-N-(1-methoxymethyl)ethylamine In Examples 10 to 22, the process is carried out analogously to Example 6, but with the following modified reaction conditions: 105 g (0.5 mol) of N-(2'-methyl-6'-ethyl-phen-1'-yl)-N-(1-methoxymethyl)ethylideneamine, 1.7 mg (0.0025 mmol) of [Ir(1,5-cyclooctadiene)Cl]$_2$, 3.8 mg (0.0059 mmol) of {(R)-1-[(S)-2-diphenylphosphino)ferrocenyl]}ethyl-di(3,5-dimethylphenyl)phosphine, 70 mg (0.189 mmol) of tetrabutylammonium iodide, 80 bar of hydrogen and 50° C. The acids used and the results of the respective tests are shown in Table 1.

TABLE 1

| Example | acid (g) | time [hrs] | conversion [%] | ee [%] |
|---|---|---|---|---|
| 10 | CH3COOH (1 g) | 16 | 100 | 70 (S) |
| 11 | Cl2CHCOOH (1 g)* | 1.5 | 100 | 75 (S) |
| 12 | Cl3CCOOH (1 g)* | 1.75 | 100 | 76 (S) |
| 13 | CH3COOH (10 g) | 2 | 100 | 76 (S) |
| 14 | CH3(CH2)3COOH (10 g) | 3 | 100 | 76 (S) |
| 15 | CH3(CH2)4COOH (10 g) | 16 | 100 | 76 (S) |
| 16 | (CH3)2CHCH2COOH (10 g) | 25 | 100 | 76 (S) |
| 17 | C6H5CH2COOH (10 g) | 8 | 95 | 76 (S) |
| 18 | C6H5COOH (10 g) | 19 | 90 | 75 (S) |
| 19 | CH3SO3H (1 g) | 2.5 | 100 | 76 (S) |
| 20 | CH3P(O)(OH)2 (1 g) | 2 | 100 | 76 (S) |
| 21 | HOOC(CH2)2COOH (10 g)** | 20 | 90 | 74 (S) |
| 22 | HOOC(CHOH)2COOH (10 g)** | 22 | 91 | 72 (S) |

*)dissolved in 2 ml of isopropanol
**)suspension in 10 ml of isopropanol

EXAMPLE 23

Preparation of N-(2'-methyl-6'-ethyl-phen-1'-yl)-N-(1-methoxymethyl)ethylamine The process is carried out analogously to Example 13, but using the following ligand: 4.3 mg (0.0059 mmol) of {(R)-1-[(S)-2-diphenylphosphino)ferrocenyl]}ethyl-di(3,5-dimethyl-4-N,N-dipropylaminophenyl)phosphine. The reaction time is 3.5 hours, the conversion: 100%, the enantiomeric purity 83% (S).

EXAMPLE 24

Preparation of N-(2'-methyl-6'-ethyl-phen-1'-yl)-N-(1-methoxymethyl)ethylamine The process is carried out analogously to Example 13, but using the following ligand: 4.2 mg (0.0059 mmol) of {(R)-1-[(S)-2-diphenylphosphino)ferrocenyl]}ethyl-di(3,5-diisopropyl-4-N,N-dimethylaminophenyl)phosphine. The reaction time is 24 hours, the conversion: 98%, the enantiomeric purity 66% (S).

EXAMPLE 25

Preparation of N-(2'-methyl-6'-ethyl-phen-1'-yl)-N-(1-methoxymethyl)ethylamine The process is carried out analogously to Example 13, but using the following ligand: 5.0 mg (0.0059 mmol) of {(R)-1-[(S)-2-diphenylphosphino)ferrocenyl]}ethyl-di(3,5-diisopropyl-4-N,N-dibenzylylaminophenyl)phosphine. The reaction time is 22 hours, the conversion: 99.5%, the enantiomeric purity 63% (S).

EXAMPLE 26

Preparation of N-(2'-methyl-6'-ethyl-phen-1'-yl)-N-(1-methoxymethyl)ethylamine The process is carried out analogously to Example 13, but using the following ligand: 4.8 mg (0.0059 mmol) of {(R)-1-[(S)-2-diphenylphosphino)ferrocenyl]}ethyl-di(3,5-dimethyl-4-N,N-dibenzylylaminophenyl)phosphine. The reaction time is 24 hours, the conversion: 85%, the enantiomeric purity 76% (S).

EXAMPLE 27

Preparation of N-(2'-methyl-6'-ethyl-phen-1'-yl)-N-(1-methoxymethyl)ethylamine The process is carried out analogously to Example 13, but using the following ligand: 4.1 mg (0.0059 mmol) of {(R)-1-[(S)-2-diphenylphosphino)ferrocenyl]}ethyl-di(3,5-dimethyl-4-(1'-pyrrolo)phenyl)phosphine. The reaction time is 3 hours, the conversion: 100%, the enantiomeric purity 69% (S).

EXAMPLE 28

Preparation of N-(2'-methyl-6'-ethyl-phen-1'-yl)-N-(1-methoxymethyl)ethylamine The process is carried out analogously to Example 13, but using the following ligand: 4.6 mg (0.0059 mmol) of {(R)-1-[(S)-2-diphenylphosphino)ferrocenyl]}ethyl-di(3,5dimethyl-4-N,N-dipentylaminophenyl)phosphine. The reaction time is 21 hours, the conversion: 90%, the enantiomeric purity 82.5% (S).

EXAMPLE 29

Preparation of N-(2'-methyl-6'-ethyl-phen-1'-yl)-N-(1-methoxymethyl)ethylamine The process is carried out analogously to Example 13, but using the following ligands: 4.0 mg (0.0059 mmol) of {(R)-1-[(S)-2-diphenylphosphino)ferrocenyl]}ethyl-di(3,5-dimethyl-4-N,N-dimethylaminophenyl)phosphine. The reaction time is 1 hour, the conversion: 100%, the enantiomeric purity 80% (S).

EXAMPLE 30

Preparation of N-benzyl-N-(1-phenylethyl)amine

The process is carried out as in Example 8 but the reaction conditions are modified as follows: 0.636 g (4.8 mmol) of N-benzyl-N-(1-phenylethylidene)amine, 3.2 mg (0.0048 mmol) of [Ir(1,5-cyclooctadiene)Cl]$_2$, 4.5 mg (0.01 mmol) of 1,4-bis(diphenylphosphino)butane (ligand) and 30 mg (0.08 mmol) of tetrabutylammonium iodide, 2 ml of acetic acid, 5 ml of toluene, 40 bar of hydrogen, reaction temperature: 25° C. The reaction time is 2 hours, the conversion is complete.

EXAMPLE 31

Preparation of N-(2'-methyl-6'-ethyl-phen-1'-yl)-N-(1 1-methoxymethyl)ethylamine The process is carried out analogously to Example 13, but using the following ligand: 4.1 mg (0.0059 mmol) of {(R)-1-[(S)-2-di(4-methoxyphenyl)phosphino)ferrocenyl]}ethyl-di(3,5-dimethyl-4-N,N-dimethylaminophenyl)phosphine.

The reaction time is 3.5 hours, the conversion: 100%, the enantiomeric purity 76% (S).

EXAMPLE 32

Preparation of N-(2'-methyl-6'-ethyl-phen-1'-yl)-N-(1-methoxymethyl)ethylamine

The process is carried out analogously to Example 13, but using the following catalyst precursors instead of the in situ catalyst: 10.4 mg (0.01 mmol) of [Ir(1,5-cyclooctadiene)-({(R)-1-[(S)-2-diphenylphosphino)ferrocenyl]}ethyl-di(3,5dimethylphenyl)phosphine)]-BF$_4$, 135 mg (0.365 mmol) of tetrabutylammonium iodide; 0.3 liter steel autoclave. The reaction time is 45 min, the conversion: 100%, the enantiomeric purity 78% (S).

EXAMPLE 33

Preparation of N-(2'-methyl-6'-ethyl-phen-1'-yl)-N-(1-methoxymethyl)ethylamine

The process is carried out analogously to Example 13, but using the following catalyst precursors instead of the in situ catalyst: 9.9 mg (0.01 mmol) of [Ir(1,5-cyclooctadiene)-({(R)-1-[(S)-2-diphenylphosphino)ferrocenyl]}ethyl-di(3,5-dimethylphenyl)phosphine)Cl], 135 mg (0.365 mmol) of tetrabutylammonium iodide; 0.3 liter steel autoclave. The reaction time is 35 min, the conversion: 100%, the enantiomeric purity 77.8% (S).

EXAMPLE 34

Preparation of N-(2',6'-dimethylphen-1'-yl)-N-(1-methoxymethyl)ethylamine

The process is carried out as in Example 6 but the reaction conditions are modified as follows: 514 g (2.6 mol) of N-(2',6'-dimethylphen-1'-yl)-N-(1-methoxymethyl)ethylamine, 77 mg (0.115 mmol) of [Ir(1,5-cyclooctadiene)Cl]$_2$, 214 mg (0.27 mmol) of {(R)-1-[(S)-2-diphenylphosphino)ferrocenyl]}ethyl-di(3,5-dimethyl-4-N,N-dipropylaminophenyl)phosphine, 3.5 g (9.5 mmol) of tetrabutylammonium iodide, 50 ml of acetic acid, 80 bar of hydrogen, temperature: 50–60° C. The reaction time is 2.5 hours, the conversion: 100%, the enantiomeric purity 78.9% (S).

EXAMPLE 35

Preparation of N-(2',6'-dimethylphen-1'-yl)-N-(1-methoxymethyl)ethylamine

The process is carried out as in Example 33 but the reaction conditions are modified as follows:

5 ml (0.024 mol) of N-(2',6'-dimethylphen-1'-yl)-N-(1-methoxymethyl)ethylamine, 10.2 mg (0.015 mmol) of [Ir(1,5-cyclooctadiene)Cl]$_2$, 21.5 mg (0.033 mmol) of {(R)-1-[(S)-2-diphenylphosphino)ferrocenyl]}ethyl-di(3,5-dimethylphenyl)phosphine, 50 mg (0.135 mmol) of tetrabutylammonium iodide, 2 ml of acetic acid, 80 bar of hydrogen, temperature: 50–60° C., 50 ml small autoclave. The reaction time is 1 hour, the conversion: 100%, the enantiomeric purity 56.2% (S).

EXAMPLE 36

The procedure followed is analogous to Example 6 but with the following modified reaction conditions.

31 kg (148.3 mol) of N-(2'-methyl-6'-ethyl-phen-1'-yl)-N-(1-methoxymethyl)ethylideneamine are placed in a 50 liter steel autoclave, followed by the addition of 500 mg (0.744 mmol) of [Ir(1,5-cyclooctadiene)Cl]$_2$, 1.15 g (1.8 mmol) of {(R)-1-[(S)-2-diphenylphosphino)ferrocenyl]}ethyl-di(3,5-dimethylphenyl)phosphine, 22.5 g (61 mmol) of tetrabutylammonium iodide and 3 liters of acetic acid. The hydrogen pressure is 75 bar, the reaction temperature 50° C. After a reaction time of 13 hours the conversion is complete. The ee is 75% (S).

EXAMPLE 37

Preparation of S-2-chloro-N-(2,6-dimethylphenyl)-N-(2-methoxy-1-methylethyl)-acetamide With stirring and while passing nitrogen through the mixture, 433 g (5.48 mol) of pyridine are added dropwise at 15–20° C. in the course of 25 minutes to a solution of 883 g (4.57 mol) of S-2,6-dimethyl-N-(2-methoxy-1-methylethyl)-aniline (ee 78.2%) in 1.8 liters of toluene. Then, with ice-cooling at 15–20° C., 547 g (4.84 mol) of chloroacetyl chloride are added dropwise thereto in the course of 1.5 hours. When the dropwise addition is complete, the suspension so obtained is stirred for a further 1.5 hours at room temperature. For working-up, the reaction mixture is poured onto 2 liters of water and extracted twice using 200 ml of toluene each time. The organic phases are combined, washed once with 300 ml of 2N hydrochloric acid, twice using 300 ml of saturated sodium chloride solution each time and once with 600 ml of saturated sodium hydrogen carbonate solution, dried over sodium sulfate and filtered, and the solvent is removed in vacuo. For purification, the crude product so obtained is subjected to fractional distillation. B.p.$_{0.3}$ 138–140° C.; ee 78.1%.

EXAMPLE 38

Preparation of S-2-chloro-N-(2-ethyl-6-methylphenyl)-N-(2-methoxy-1-methylethyl)-acetamide 10.52 kg (50.7 mol) of S-2-ethyl-N-(2-methoxy-1-methylethyl)-6-methylaniline (ee 80.9%; [a]$_D^{20}$: 16.43 c: 2.6112 in hexane) are placed in 20 liters of toluene, and at 10° C. 4812 g (60.8 mol) of pyridine are added. With ice-cooling at 10–20° C., 6073 g (53.7 mol) of chloroacetyl chloride are then added dropwise in the course of 2.5 hours to the reaction solution so obtained. When the addition is complete, the resulting suspension is stirred at room temperate for 16 hours. For working-up, the reaction mixture is poured onto 20 liters of water and the resulting emulsion is stirred vigorously for 10 minutes. After removal of the organic phase, the aqueous phase is extracted once with 10 liters of hexane. The combined organic phases are washed once with 10 liters of water, once with 5 liters of 2N hydrochloric acid and once with 10 liters of water, dried over sodium sulfate and filtered, and concentrated in a rotary evaporator. For purification, the crude product so obtained is subjected to fractional distillation. B.p.$_{0.1}$ 135–140° C.; ee 81.0%; [a]$_D^{20}$: −6.53 c: 2.2364 in hexane.

EXAMPLE 39

40 kg (194 mol) of MEA-imine of formula (Vb) are drawn into an inert container towards a closed vacuum and the residual vacuum is broken with nitrogen. The contents of the container are then introduced under pressure into an inert 50 liter loop reactor (loop reactor manufactured by Buss). After a mixture of 0.14 g (2.08 10$^{-4}$ mol) of [Ir{COD}Cl]$_2$
0.27 g (4.23 10$^{-4}$ mol) of ligand {(R)-1-[(S)-2-diphenylphosphino)ferrocenyl]}ethyl-di(3,5-dimethyl-phenyl)phosphine and
6.20 g (1.66 10$^{-2}$ mol) of TBAI (tetrabutylammonium iodide), has been introduced into the reactor via a solids sluice, rinsing is carried out with 4.1 kg (68 mol) of acetic acid (anhydrous) and the reactor is depressurised. The reactor is then twice pressurised with hydrogen to 5 bar and depressurised. The accompanying heating of the reactor is set to Ta=50° C. The loop reactor is then pressurised to 80 bar with hydrogen and the circulating pump is switched on. A rapid absorption of hydrogen is observed which achieves the theoretical hydrogen consumption after about 1–2 hours. When no further absorption of hydrogen can be detected, the reactor contents are cooled to room temperature and depressurised. The reactor is then rendered inert with nitrogen and the contents are removed. The hydrogenated solution is worked up by distillation and the product is isolated in a yield of 98%.

EXAMPLE 40

The process is carried out as in Example 6, but the reaction conditions are modified as follows: in a 11-reaction vessel 413 g (2,004 mmol) of the imine, 2.8 mg of the iridium compound, 6.4 mg of the diphosphine ligand and 124.2 mg of the iodide are used. Instead of 2 ml of acetic acid 0.1 g of H$_2$SO$_4$ are used.

The conversion is 100%. After isolation and purification according to Example 6 one obtains 99% of the desired product, the optical yield being 76.0% (S).

What is claimed is:

1. A process for the hydrogenation of an imine comprising:
   a). forming, with or without an inert solvent, a reaction mixture of 1) an imine, 2) an iridium catalyst 3) an acid, and 4) an ammonium chloride, bromide or iodide, or a metal chloride, bromide or iodide that is soluble in the reaction mixture,
   b) reacting the mixture with hydrogen under elevated pressure.

2. A process according to claim 1, wherein the imine contains at least one

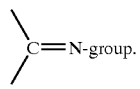
C=N-group.

3. A process according to claim 1, wherein the imine contains at least one of the groups

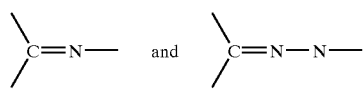

and additionally unsaturated groups

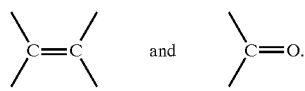

4. A process according to claim 3, wherein the free bonds are saturated with hydrogen or organic radicals having from 1 to 22 carbon atoms or organic hetero radicals having from 1 to 20 carbon atoms, and at least one hetero atom from the group O, S, N and P; or the
nitrogen atom of the group

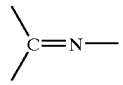

is saturated with NH$_2$ or a primary amino group having from 1 to 22 carbon atoms or a secondary amino group having from 2 to 40 carbon atoms.

5. A process according to claim 1, wherein an aldimine, ketimine or hydrazone is hydrogenated.

6. A process according to claim 5, wherein the imine is an imine of formula I

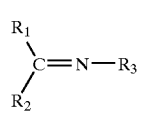

(I)

which is hydrogenated to form an amine of formula II

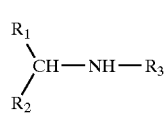

(II)

wherein
  R$_3$ is linear or branched C1–C12alkyl, cycloalkyl having from 3 to 8 ring carbon atoms; heterocycloalkyl bonded via a carbon atom and having from 3 to 8 ring atoms and 1 or 2 hetero atoms from the group O, S and NR$_6$; a C$_7$–C$_{16}$aralkyl bonded via an alkyl carbon atom, or C$_1$–C$_{12}$alkyl substituted by the mentioned cycloalkyl or heterocycloalkyl or heteroaryl;
  or wherein
  R$_3$ is C$_6$–C$_{12}$aryl, or C$_4$–C$_{11}$heteroaryl bonded via a ring carbon atom and having 1 or 2 hetero atoms in the ring; R$_3$ being unsubstituted or substituted by —CN, —NO$_2$, F, Cl, C$_1$–C$_{12}$alkyl, C$_1$–C$_{12}$alkoxy, C$_1$–C$_{12}$alkylthio, C$_1$–C$_6$haloalkyl, —OH, C$_6$–C$_{12}$-aryl or -aryloxy or -arylthio, C$_7$–C$_{16}$-aralkyl or -aralkoxy or -aralkylthio, secondary amino having from 2 to 24 carbon atoms, —CONR$_4$R$_5$ or by —COOR$_4$, and the aryl radicals and the aryl groups in the aralkyl, aralkoxy and aralkylthio in turn being unsubstituted or substituted by —CN, —NO$_2$, F, Cl, C$_1$–C$_4$-alkyl, -alkoxy or -alkylthio, —OH, —CONR$_4$R$_5$ or by —COOR$_4$;
  R$_4$ and R$_5$ are each independently of the other hydrogen, C$_1$–C$_{12}$alkyl, phenyl or benzyl, or
  R$_4$ and R$_5$ together are tetra- or penta-methylene or 3-oxapentylene; R$_6$ has independently the same meaning as given for R$_4$;
  R$_1$ and R$_2$ are each independently of the other a hydrogen atom, C$_1$–C$_{12}$alkyl or cycloalkyl having from 3 to 8 ring carbon atoms, each of which is unsubstituted or substituted by —OH, C$_1$–C$_{12}$alkoxy, phenoxy, benzyloxy, secondary amino having from 2 to 24 carbon atoms, —CONR$_4$R$_5$ or by —COOR$_4$; C$_6$–C$_{12}$aryl or C$_7$–C$_{16}$aralkyl that is unsubstituted or substituted as R$_3$, or —CONR$_4$R$_5$ or —COOR$_4$, wherein R$_4$ and R$_5$ are as defined hereinbefore; or
  R$_3$ is as defined hereinbefore and R$_1$ and R$_2$ together are alkylene having from 2 to 5 carbon atoms that is optionally interrupted by 1 or 2 —O—, —S— or —NR₆— radicals, and/or unsubstituted or substituted by ═O or as R₁ and R₂ above in the meaning of alkyl, and/or condensed with benzene, pyridine, pyrimidine, furan, thiophene or pyrrole; or R₂ is as defined hereinbefore and R₁ and R₃ together are alkylene having from 2 to 5 carbon atoms that is optionally interrupted by 1 or 2 —O—, —S— or —NR₆— radicals, and/or unsubstituted or substituted by ═O or as R₁ and R₂ above in the meaning of alkyl, and/or condensed with benzene, pyridine, pyrimidine, furan, thiophene or pyrrole.

7. A process according to claim 5, wherein R₁ and R₂ as heteroaryl form a 5- or 6-membered ring having 1 or 2 identical or different hetero atoms.

8. A process according to claim 5, wherein R₁ and R₂ as heteroaryl-substituted alkyl are derived from a 5- or 6-membered ring having 1 or 2 identical or different hetero atoms.

9. A process according to claim 5, wherein R₁ and R₂ as heterocycloalkyl or as hetero-cycloalkyl-substituted alkyl contain from 4 to 6 ring atoms and 1 or 2 identical or different hetero atoms from the group O, S and NR₆, wherein R₆ is hydrogen, C₁–C₁₂alkyl, phenyl or benzyl.

10. A process according to claim 5, wherein R₁, R₂ and R₃ as alkyl are unsubstituted or substituted C₁–C₆alkyl.

11. A process according to claim 5, wherein R₁, R₂ and R₃ as unsubstituted or substituted cycloalkyl contain from 3 to 6 ring carbon atoms.

12. A process according to claim 5, wherein R₁, R₂ and R₃ as aryl are unsubstituted or substituted naphthyl or phenyl, and R₁, R₂ and R₃ as aralkyl are unsubstituted or substituted phenylalkyl having from 1 to 10 carbon atoms in the alkylene.

13. A process according to claim 5, wherein R₁ and R₂ together or R₁ and R₃ together form, with the carbon atom or the —N═C group to which they are bonded, respectively, a 5- or 6-membered ring.

14. A process according to claim 5, wherein formula I R₃ is 2,6-di-C₁–C₄alkylphen-1-yl, R₁ is C₁–C₄alkyl, and R₂ is C₁–C₄alkyl, C₁–C₄alkoxymethyl or C₁–C₄alkoxyethyl.

15. A process according to claim 14, wherein R₃ is 2,6-dimethylphen-1-yl or 2-methyl-6-ethylphen-1-yl, R₁ is ethyl or methyl, and R₂ is methoxymethyl.

16. A process according to claim 6, wherein the imine corresponds to the formula

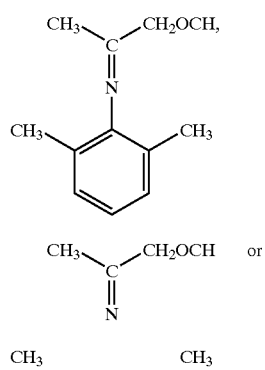

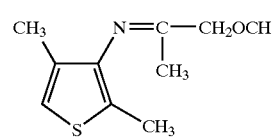

17. A process according to claim 1, wherein the iridium catalyst is a homogeneous catalyst that is substantially soluble in the reaction medium.

18. A process according to claim 1, wherein the catalyst corresponds to the formula III, IIIa, IIIb, IIIc or IIId

[XIrYZ]     (III),

[XIrY]⁺A⁻     (IIIa),

[YIrZ₄]⁻M⁺     (IIIb),

[YIrHZ₂]₂     (IIIc),

[YIrZ₃]₂     (IIId), wherein X is two olefin ligands or a diene ligand, Y is a diphosphine having secondary phosphine groups (a) the phosphine groups of which are bonded to different carbon atoms of a carbon chain having from 2 to 4 carbon atoms, or (b) the phosphine groups of which are either bonded directly or via a bridge group —CR_aR_b— in the ortho positions of a cyclopentadienyl ring or are each bonded to a cyclopentadienyl ring of a ferrocenyl, or (c) one phosphine group of which is bonded to a carbon chain having 2 or 3 carbon atoms and the other phosphine group of which is bonded to an oxygen atom or a nitrogen atom bonded terminally to that carbon chain, or (d) the phosphine groups of which are bonded to the two oxygen atoms or nitrogen atoms bonded terminally to a C₂-carbon chain;

with the result that in the cases of (a), (b), (c) and (d) a 5-, 6- or 7-membered ring is formed together with the Ir atom, the radicals Z are each independently of the other(s) Cl, Br or I, A⁻ is the anion of an oxy or complex acid, and M⁺ is an a metal cation or quaternary ammonium, and R_a and R_b are each independently of the other hydrogen, C₁–C₈alkyl, C₁–C₄fluoroalkyl, phenyl or benzyl or are phenyl or benzyl having from 1 to 3 C₁–C₄alkyl or C₁–C₄alkoxy substituents.

19. A process according to claim 18, wherein the diphosphine Y contains at least one chiral carbon atom.

20. A process according to claim 18, wherein X as an olefin ligand is branched or linear C₂–C₁₂alkylene; and X as a diene ligand is an open-chain or cyclic diene having from 4 to 12 carbon atoms.

21. A process according to claim 18, wherein the secondary phosphine groups contain two identical or different radicals from the following group: linear or branched C₁–C₁₂alkyl; unsubstituted or C₁–C₆alkyl-orC₁–C₆alkoxy-substituted C₅–C₁₂cycloalkyl, C₅–C₁₂cycloalkyl-CH₂—, phenyl or benzyl; or phenyl or benzyl substituted by halogen (e.g. F, Cl or Br), C₁–C₆haloalkyl, (C₁–C₁₂alkyl)₃Si, (C₆H₅)₃Si, C₁–C₆haloalkoxy (e.g. trifluoromethoxy), —NH₂, phenyl₂N—, benzyl₂N—, morpholinyl, piperidinyl, pyrrolidinyl, (C₁–C₁₂alkyl)₂N—, -ammonium-X₁—, —SO₃M₁, —CO₂M₁, —PO₃M₁ or by —COO—C₁–C₆alkyl (e.g. —COOCH₃), wherein $M_1$ is an alkali metal or hydrogen and $X_1^-$ is the anion of a monobasic acid.

22. A process according to claim 18, wherein the diphosphine Y is of the formula:

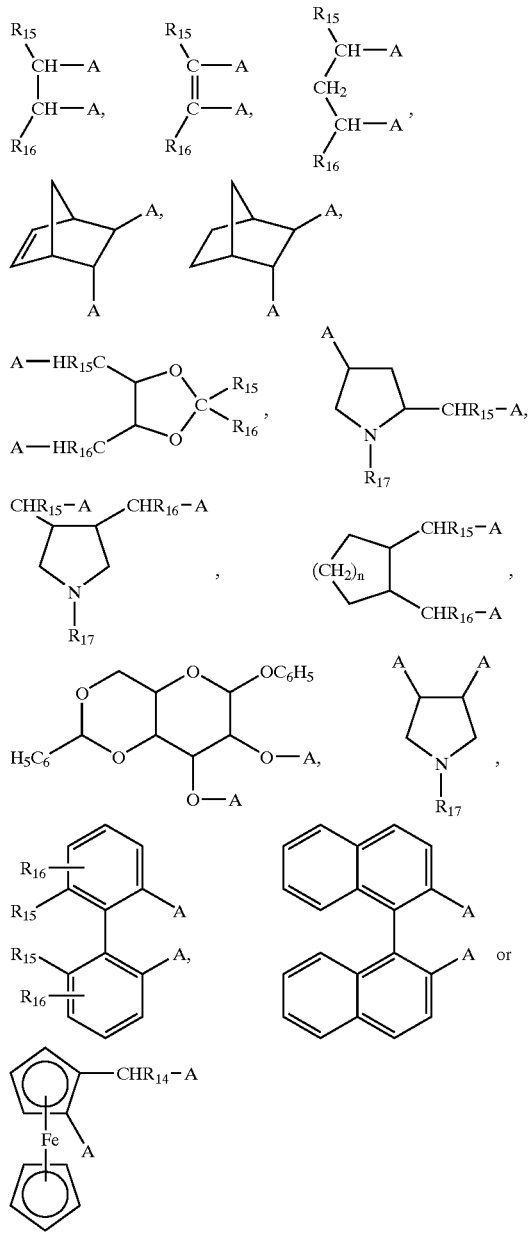

wherein
R₁₅ and R₁₆ are each independently of the other hydrogen, $C_1$–$C_4$alkyl, phenyl, benzyl, or phenyl or benzyl having from 1 to 3 $C_1$–$C_4$alkyl or $C_1$–$C_4$alkoxy substituents,
R₁₄ is hydrogen, $C_1$–$C_4$alkyl, phenyl, benzyl, or phenyl or benzyl having from 1 to 3 $C_1$–$C_4$alkyl or $C_1$–$C_4$alkoxy substituents,
R₁₇ is hydrogen, $C_1$–$C_4$alkyl, phenyl, benzyl $C_1$–$C_6$alkoxy-CO—, $C_1$–$C_6$alkyl-CO—,
Phenyl-CO—, naphthyl-CO— or $C_1$–$C_4$alkylNH—CO—,
A may be identical or different groups —PR₂, wherein R is $C_1$–$C_6$alkyl, cyclohexyl, phenyl, benzyl, or phenyl or benzyl having from 1 to 3 $C_1$–$C_4$alkyl, $C_1$–$C_4$alkoxy, —CF₃ or partially or fully fluorinated $C_2$–$C_4$alkoxy substituents, and
N is 0, 1 or 2.

23. A process according to claim 18, wherein the diphosphine Y is
{(R)-1-[(S)-2-diphenylphosphino)ferrocenyl]}ethyl-di(3,5-dimethyl-phenyl)phosphine
{(R)-1-[(S)-2-diphenylphosphino)ferrocenyl]}ethyl-di(3,5-dimethyl-4-N,N-dipropyl-aminophenyl)phosphine
{(R)-1-[(S)-2-diphenylphosphino)ferrocenyl]}ethyl-di(3,5-diisopropyl-4-N,N-dimethylaminophenyl)phosphine
{(R)-1-[(S)-2-diphenylphosphino)ferrocenyl]}ethyl-di(3,5-dimethyl-4-N,N-dibenzylylaminophenyl)phosphine
{[(R)-1-[(S)-2-diphenylphosphino)ferrocenyl]}ethyl-di (3,5-dimethyl-4-N,N-dibenzylylaminophenyl) phosphine
{(R)-1-[(S)-2-diphenylphosphino)ferrocenyl]}ethyl-di(3,5-dimethyl-4-(1'-pyrrolo)-phenyl)phosphine
{[(R)-1-[(S)-2-diphenylphosphino)ferrocenyl]}ethyl-di (3,5-dimethyl-4-N,N-dipentyl-aminophenyl)phosphine
{[(R)-1-[(S)-2-diphenylphosphino)ferrocenyl]}ethyl-di (3,5-dimethylaminophenyl)phosphine
1,4-bix(diphenylphosphino)butane or
{[(R)-1-[(S)-2-di(4-methoxyphenyl)phosphino) ferrocenyl]}ethyl-di(3,5-dimethyl-4-N,N-dimethylaminophenyl)phosphine.

24. A process according to claim 1, wherein the ammonium chloride, bromide or iodide, or the emtal chloride, bromide or iodide that is soluble in the reaction mixture, is used in an amount of from 0.01 to 200 mol %, based on the iridium catalyst.

25. A process according to claim 1, wherein the metal chloride, bromide or iodide used is an alkali metal chloride, bromide or iodide.

26. A process according to claim 1, wherein the ammonium or alkali metal chloride, bromide or iodide is a tetraalkylammonium chloride, bromide or iodide having from 1 to 6 carbon atoms in the alkyl groups or in the case of an alkali metal chloride, bromide or iodide is a sodium, lithium or potassium chloride, bromide or iodide.

27. A process according to claim 1, wherein the acid is an inorganic or organic acid.

28. A process according to claim 1, wherein the acid is used in an amount of from 0.001 to 50% by weight, preferably 0.1 to 50% by weight, based on the imine.

29. A process according to claim 27, wherein the organic acid is an aliphatic or aromatic carboxylic acid, sulfonic acid or phosphorus (V) acid.

30. A process according to claim 27, wherein the organic acid is acetic acid, propionic acid, trifluoroacetic acid, chloroacetic acid or methanesulfonic acid, and the inorganic acid is $H_2SO_4$.

31. A process according to claim 1, wherein the molar ratio of the imine to the iridium catalyst is from 500 000 to 20.

32. A process according to claim 1, wherein the reaction temperature is from −20 to 100° C.

33. A process according to claim 1, wherein the hydrogen pressure is from 5 to 150 bar.

34. A process according to claim 2, wherein the hydrogenation is carried out in a loop reactor.

35. A process according to claim 1, wherein an aldimine or a ketimine formed in situ before or during the hydrogenation is hydrogenated.

36. A process for the preparation of a compound of the formula

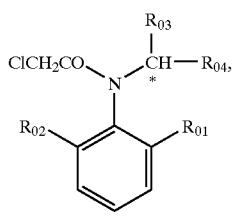

(IV)

wherein $R_{01}$, $R_{02}$ and $R_{03}$ are each independently of the other $C_1$–$C_4$alkyl, and $R_{04}$ is $C_1$–$C_4$alkyl or $C_1$–$C_4$alkoxymethyl or $C_1$–$C_4$alkoxyethyl, comprising:

a). forming, with or without an inert solvent, a reaction mixture of 1) an imine of the formula

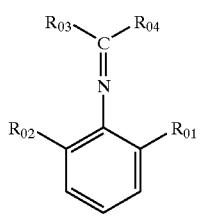

(V)

2) an iridium catalyst, 3) an acid, and 4) an ammonium chloride, bromide or iodide, or a metal chloride, bromide or iodide that is soluble in the reaction mixture;

b). reacting the mixture with hydrogen under elevated pressure to form an amine of the formula

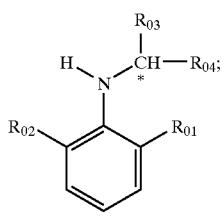

(VI)

and (c). reaction thereof with the compound of formula

ClCH$_2$CO—Cl    (VII).

37. A process according to claim 36, wherein the imine used is a compound of the formula

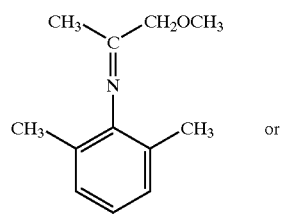

(Va)

or

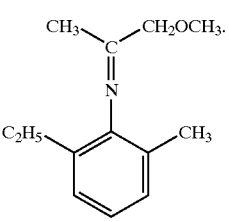

(Vb)

* * * * *